(12) United States Patent
Consoli et al.

(10) Patent No.: US 10,105,301 B2
(45) Date of Patent: Oct. 23, 2018

(54) COMPOSITION FOR COLOURING HAIR

(71) Applicant: Beauty & Business S.p.A., Milan (IT)

(72) Inventors: Antonio Consoli, Urgnano (IT); Katiuscia Grevalcuore, Urgnano (IT)

(73) Assignee: Beauty & Business S.p.A., Milan (IT)

( * ) Notice: Subject to any disclaimer, the term of this patent is extended or adjusted under 35 U.S.C. 154(b) by 29 days.

(21) Appl. No.: 15/618,107

(22) Filed: Jun. 8, 2017

(65) Prior Publication Data

US 2017/0354581 A1 Dec. 14, 2017

(30) Foreign Application Priority Data

Jun. 9, 2016 (IT) .................. 102016000059348

(51) Int. Cl.
*A61Q 5/10* (2006.01)
*A61K 8/49* (2006.01)
*A61K 8/41* (2006.01)
*A61Q 5/06* (2006.01)

(52) U.S. Cl.
CPC ............... *A61K 8/49* (2013.01); *A61K 8/411* (2013.01); *A61K 8/4926* (2013.01); *A61Q 5/065* (2013.01); *A61Q 5/10* (2013.01); *A61K 2800/88* (2013.01)

(58) Field of Classification Search
CPC ... A61Q 5/10; A61K 8/49; A61K 8/55; A61K 2800/42; A61K 2800/43; A61K 2800/88
See application file for complete search history.

(56) References Cited

FOREIGN PATENT DOCUMENTS

WO WO 2016/026710 A1 * 2/2016 ............... A61Q 5/06

OTHER PUBLICATIONS

STIC Search Report dated Jul. 22, 2017.*

* cited by examiner

*Primary Examiner* — Eisa B Elhilo
(74) *Attorney, Agent, or Firm* — Greer, Burns & Crain, Ltd.; Gregory P. Einhorn

(57) ABSTRACT

The present invention describes a composition for coloring hair, comprising at least one dye having the formula (I) and at least one dye having the formula (II):

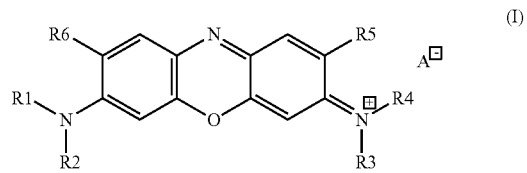

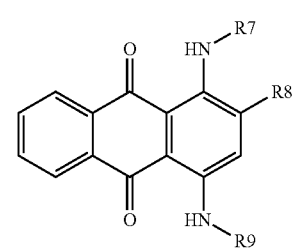

where the groups are defined in the description.

The composition provides hair colorings stable and brilliant at various pH values and also resistant to washing.

23 Claims, No Drawings

COMPOSITION FOR COLOURING HAIR

CROSS REFERENCE TO RELATED APPLICATIONS

This U.S. utility patent application claims benefit of priority under 35 U.S.C. 119(a) to Italian patent application no. 102016000059348, filed Jun. 9, 2016. The contents of this application is expressly incorporated herein by reference in its entirely for all purposes.

FIELD OF INVENTION

The present invention relates to the cosmetic field, in particular to the field of hair dyes.

PRIOR ART

Dyeing or colouring of hair is currently affected by the most varied trends. Whereas, in the past, hair was dyed mainly to cover up areas of grey hair, nowadays there is an increased demand for fashion-based hair colour as an expression of personality. Two hair dye technologies are widely used. The first involves the use of oxidative dyes and an activator (oxidative hair dyes) while the second one involves the use of direct colourants.

Oxidative dyes have become extremely important in the conventional hair dye sector. The dye is created by a reaction between primary intermediates and couplers in the presence of an oxidant. Oxidising dyes offer the best performance in terms of resistance to washing and are therefore called permanent dyes.

Dyes that involve the use of direct colourants have become particularly widespread in recent years both because of increased problems of sensitisation owing to the colourants in oxidising dyes and for the possibility to create with direct colourants particularly vivid shades, which can not be obtained using oxidising dyes. In fact, when using particular direct colourants with combinations of Magenta, Blue and Yellow, it is possible to obtain, besides natural colourings such as black, brown, golden and copper, also "crazy" colourings such as blue, green and violet (such as, for example, PANTONE blue PQ-3591 C, PANTONE green 3405C, PANTONE violet PQ-2592C and PANTONE 266 C). In the technical field of the invention, "crazy" colouring means colours with intense tone without level, able to provide to the hair a non-natural colouring.

Direct colourants can be classified in anionic, cationic or non-ionic according to whether or not they can be ionised.

Dyes that can be created using direct colourants can be defined, according to their ability to withstand washing, as semi-permanent or temporary. Semi-permanent dyes can withstand up to 8 washes, and temporary ones up to 2 washes, see table 1 below:

TABLE 1

|  | TEMPORARY | SEMI-PERMANENT | SEMI-PERMANENT | PERMANENT |
|---|---|---|---|---|
| DURATION PROPERTY | 1-2 shampoos | 6-8 shampoos | 6-8 weeks | Permanent |
| LIGHTENING EFFECT | No | No | No | Yes |
| GREY HAIR COVERAGE | No | For people with up to 30% grey hair (first greys) | For people with up to 50% grey hair | For people with 100% grey hair |
| COLOURING PROPERTY | Only on bleached hair or to add tone | All shades with or without bleach | All shades with or without bleach | Lighter, equivalent or darker shades With/without highlights |
| FINISHED PRODUCT | Ready-to-use | Ready-to-use | Mix before use: 1 coloured product + 1 to 3 parts of activator | Mix before use: 1 coloured product + 1 to 3 parts of activator |

In recent years, cationic or basic direct colourants have been used a lot. These colourants are able to bind to the hair much more efficiently than anionic or non-ionic colourants. Cationic colourants are better able to withstand washing than the other two categories, with the result that semi-permanent dyes can also be created.

In the last decade of the 20th century, two particularly important cationic colourants were brought onto the cosmetics market, named according to the INCI nomenclature (European Community Decision 2006/257/EC as amended—International Nomenclature Cosmetic Ingredients), Basic Red 51 and Basic Yellow 87. EP 0681464 mentions the chemical structures of Basic Red 51 (BR51) and Basic Yellow 87 (BY87). Basic Red 51 and Yellow 87 can be combined to give colourings from intense red to orange.

The compound 1-[(2-hydroxyethyl)amino]-4-[(3-hydroxypropyl)amino]anthracene-9,10-dione, also known as Disperse blue 377, is described in DE20213695.

DE102014224838 discloses compositions for colouring hair comprising phenoxazin dyes in combination with fatty alcohols.

In 2013, BASF introduced Basic Blue 124 (BB124) (described in U.S. Pat. No. 8,268,014), thus completing the series of the three primary cationic colours with which all types of dyes (ranging from natural to crazy colours) can be formulated.

In fact, BB124 and BY87 can be combined in a formulation to obtain greens, BB124 and BR51 can be combined to obtain violet or BB124, BY87 and BR51 can be combined to obtain colours ranging from black to chestnut brown or blonde having natural tone.

To achieve greater brilliance and homogeneity between the roots and tips, it is also possible to combine BB124, BR51 and BY87 with a peroxide.

However, a main inconvenient of the combination of BB124, BR51 and BY87 is that the resulting colour changes depending on the pH. In particular, BB124 tends to provide a violet colour instead of a blue colour at high pH values.

This implies that the combination of the three colourants has to be carefully designed and prepared depending on the pH at which it will be used.

Therefore, there is a strong need of using the colourant BB124 in the widest possible range of pH, without causing a variation of the blue colouring.

In particular, the problem of variations of the colouring at different pH values is particularly relevant when it is necessary or desirable to mix the colourant composition with any other cosmetic, in particular a cosmetic product for hair, such as for example a shampoo, a lotion, a conditioner, another dyeing, a composition for hair care and maintenance or a composition for hairstyle, since such cosmetic products have different characteristic pH values which can affect the dyeing composition, thus impairing the final dyeing.

Also, BB124 is an excellent blue to use for the creation of natural colours but since it lacks brilliance it is particularly difficult to successfully formulate very vibrant "crazy" colours with a blue, green and violet tone.

It is therefore desired to provide a formulation that uses BB124 but that is able to give brilliant colours, in particular with a blue, green and violet tone, when applied to human hair.

In the past, the colourant HC Blue no 15 (Basic Blue 77) has been introduced; this is an excellent brilliant blue but unfortunately changes to green after a few washes or basic treatments and persists for a long time, and can only be removed using particular chemical treatments (it cannot even be removed by using persulfates). This green colouring that remains on the hair is particularly unattractive.

Therefore, the problem of resistance of the dyes to washing is very relevant for the formulator, who is constantly seeking combinations of raw materials that are able to improve the resistance of the colour to washing, without unattractive colour changes.

A first aim of the invention is to solve the above mentioned problems by means of a new combination of blue colourants which can be used in any cosmetic form, can be applied directly to the hair or in a ready-to-use mixture in order to create any desired shade of colour, and, most importantly, provides the same colouring result at any pH value and without unattractive colour changes due to washing.

More in particular, an aim of the invention is to provide a very versatile composition which can be used alone or in combination with any other cosmetic product, in particular any hair cosmetic product, without the different pH values of the cosmetic products affecting the characteristics of the colouring composition.

Another aim of the invention is to provide a formulation containing BB124 that is capable of giving brilliant colours, in particular with a blue, green or violet tone.

SUMMARY OF THE INVENTION

It has been found that the above-mentioned aims are achieved using a composition comprising the combination of at least two dyes having the general formula I and II:

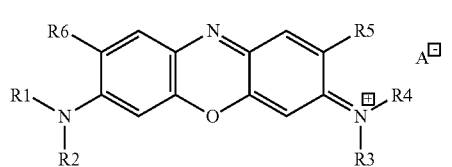

(I)

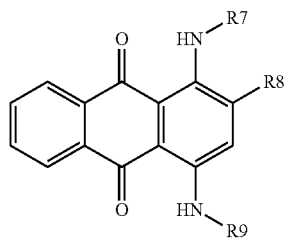

(II)

wherein:

in formula (I):

$R_1$, $R_2$, $R_3$ and $R_4$ can be a hydrogen, a $C_1$ to $C_{10}$ linear, branched, saturated or unsaturated alkyl group or an aryl group, for example phenyl or benzyl. When each of the $R_1$-$R_4$ groups is a $C_1$-$C_{10}$ alkyl chain, this can be substituted by one or more amino, imino, hydroxyl and aldehyde groups, and/or this chain can contain one or more nitrogen groups, optionally substituted by a $C_1$-$C_6$ linear or branched, saturated or unsaturated alkyl group; oxygen or keto. $R_5$ is hydrogen or a $C_1$-$C_6$ linear or branched, saturated or unsaturated alkoxy group, $R_6$ is preferably hydrogen, or alternatively a linear or branched $C_1$-$C_{10}$ alkyl group in which amino groups can be present, optionally substituted with an alkyl having 1 to 4 carbon atoms, or hydroxyl, A is a cosmetically acceptable anion, preferably colourless when applied to the hair, for example sulfate, chloride, phosphate, bromide, methanesulfonate.

In formula (II):

$R_7$, $R_8$ and $R_9$ are independently hydrogen, a $C_1$ to $C_{10}$ linear, branched, saturated or unsaturated alkyl group, an aryl group or a cyan group. When each of the $R_7$-$R_9$ groups is a $C_1$-$C_{10}$ alkyl chain, this can be substituted by one or more amino, imino, hydroxyl and aldehyde groups, and/or this chain can contain one or more nitrogen groups, optionally substituted by a $C_1$-$C_6$ linear or branched, saturated or unsaturated alkyl group; oxygen or keto, provided that when $R_8$ is H, $R_7$ and $R_9$ are not both selected from $CH_2CH_2OH$ and $CH_2CH_2CH_2OH$.

Preferably, each of $R_7$, $R_8$ and $R_9$ is independently hydrogen, methyl or linear $C_1$-$C_{10}$ alkyl, optionally substituted by one or more amino, imino, hydroxyl and aldehyde groups, and/or said chain can contain one or more nitrogen groups, optionally substituted by a $C_1$-$C_6$ linear or branched, saturated or unsaturated alkyl group; oxygen or keto. $R_8$ is preferably hydrogen or a cyan group.

Preferably, $R_1$ and $R_1$ are independently selected from hydrogen, methyl or phenyl, $R_3$ and $R_4$ are independently selected from hydrogen and saturated $C_1$-$C_6$ alkyl.

Compounds of formula (II) can be in the form of a cosmetically acceptable salt, where the anion can be, for example, sulfate, chloride, phosphate, bromide or methanesulfonate, In addition to provide a surprisingly brilliant and washing resistant blue colouring, the present invention provides the unexpected advantage of providing the expert with a single product for dyeing human hair, said colouring product which can be mixed with any hair cosmetic product having any pH, still providing the same colouring result both in terms of tone and brilliance.

The present invention will now be described in detail, also by means of examples.

DETAILED DESCRIPTION OF THE INVENTION

According to the present invention, examples of a saturated $C_1$-$C_{10}$ alkyl group are methyl, ethyl, propyl, butyl, pentyl, hexyl, heptyl, octyl, nonyl, decyl and isomers thereof.

Examples of an unsaturated alkyl group are ethenyl, propenyl, butenyl, pentenyl, hexenyl, heptenyl, octenyl, nonenyl, decenyl and isomers thereof. The double bond can occupy various positions within the chain. Several double bonds can also be present.

Examples of an aryl group are phenyl and benzyl.

Examples of compounds of formula (I) according to the present invention are:

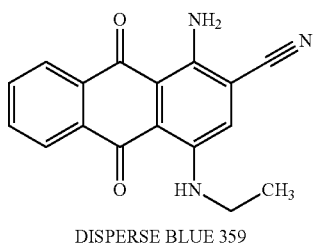

DISPERSE BLUE 359

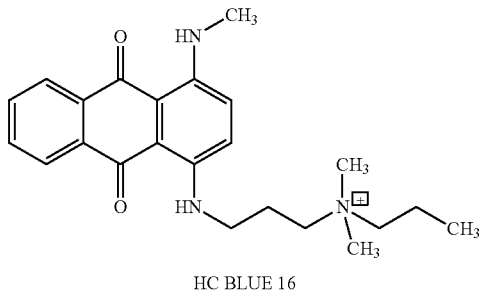

HC BLUE 16

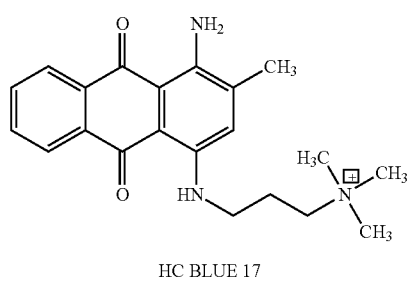

HC BLUE 17

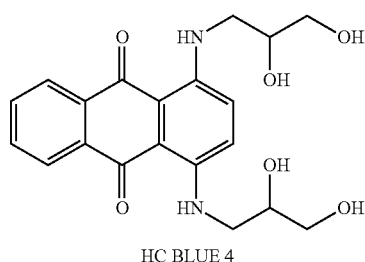

HC BLUE 4

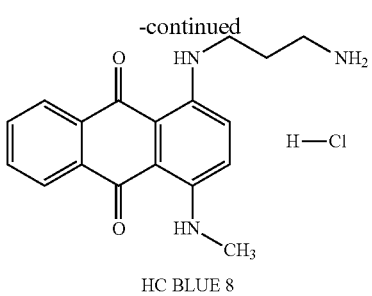

HC BLUE 8

Examples of compounds of formula (II) according to the invention are:

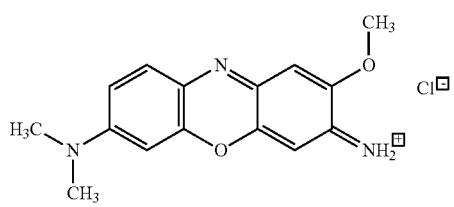

Basic Blue 124

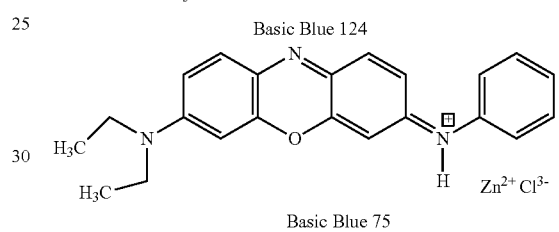

Basic Blue 75

Examples of colourants of formulas (I) and (II), defined according to the INCI nomenclature, are, for formula (I), Basic Blue 124 and Basic Blue 75, and for formula (II), are HC Blue 16, HC Blue 17 and Disperse Blue 359.

A preferred embodiment of the invention provides for the combination of the colourants Basic Blue 124 and HC Blue 16.

The total amount of the combination of the two colourants according to the invention is conventionally determined by the dye formulator. In a preferred example, this amount varies from about 0.0005 to about 20 wt. %, more preferably from about 0.001 to about 10 wt. % and even more preferably from about 0.005 to about 5.0 wt. %.

Within the context of the present invention, the expression "from about . . . to about" means that variations in the weight value between the extremes of the range, either upwards or downwards, are possible so as to substantially maintain the technical effect obtained, for example a particular shade of colour, intensity and vividness.

The combination of the colourants of formulas I and II can be used alone or in combination with other oxidising or direct colourants.

Examples of oxidative dyes, as defined according to the INCI nomenclature, comprise:
1-Acetoxy-2-Methylnaphthalene, 5-Amino-4-Chloro-o-Cresol, 4-Amino-m-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2,6-Dimethoxy-3-Hydroxypyridine, 5-Amino-2,6-Dimethoxy-3-Hydroxypyridine, 3-Amino-2,6-Dimethylphenol, 2-Amino-5-Ethylphenol, 5-Amino-4-Fluoro-2-Methylphenol Sulfate, 2-Amino-4-Hydroxyethylaminoanisole, 2-Amino-4-Hydroxyethylaminoanisole, 2-Amino-3-Hydroxypyridine, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, p-Aminophenol, 1,3-Bis-(2,4-Diaminophenoxy)propane, 4,6-Bis(2-Hydroxyethoxy)-m-Phenylenediamine, 2,6-Bis(2-Hydroxyethoxy)-3,5-Pyridinediamine, N,N-Bis(2-Hydroxyethyl)-p-Phenylenediamine, 4-Chloro-2-Aminophenol, 2-Chloro-p-Phenylenediamine, 4-Chlororesorcinol, N-Cyclopentyl-m-Aminophenol, 3,4-Diaminobenzoic Acid, 4,5-Diamino-1-((4-Chlorophenyl)-Methyl)-1H-Pyrazole Sulfate, 2,3-Diaminodihydropyrazolo Pyrazolone Dimethosulfonate, 2,4-Diaminodiphenylamine, 4,4'-Diaminodiphenylamine, 2,4-Diamino-5-Methylphenetole, 2,4-Diamino-5-Methylphenoxyethanol, 4,5-Diamino-1-Methylpyrazole, 2,4-Diaminophenol, 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, Dihydroxy-indoline, 2,6-Dimethoxy-3,5-Pyridinediamine, m-Dimethylaminophenyl-Urea, N,N-Dimethyl-p-Phenylenediamine, 2,6-Dimethyl-p-Phenylenediamine, N,N-Dimethyl-2,6-Pyridinediamine, 4-Ethoxy-m-Phenylenediamine, 3-Ethylamino-p-Cresol, 4-Fluoro-6-Methyl-m-Phenylenediamine, 1-Hexyl-4,5-Diamino-Pyrazole Sulfate, Hydroquinone, Hydroxyanthraquinoneaminopropyl-Methyl-Morpholinium Methosulfate, Hydroxybenzomorpholine, Hydroxyethoxy-Amino-pyrazolopyridine, Hydroxyethylaminomethyl-p-Aminophenol, 1-Hydroxyethyl-4,5-Diamino Pyrazole, Hydroxyethyl-2,6-Dinitro-p-Anisidine, Hydroxyethyl-3,4-Methylenedioxyaniline, Hydroxyethyl-p-Phenylenediamine, 2-Hydroxyethyl-Picramic Acid, 6-Hydroxyindole, Hydroxy-propyl-Bis(N-Hydroxyethyl-p-Phenylenediamine), Hydroxypropyl-p-Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 2-Methoxymethyl-p-Phenylenediamine, 2-Methoxy-p-Phenylenediamine, 6-Methoxy-2,3-Pyridinediamine, 4-Methoxytoluene-2,5-Diamine, p-Methylaminophenol, 4-Methylbenzyl-4,5-Diamino-Pyrazole, 2,2'-Methylenebis-4-Aminophenol, 3,4-Methylenedioxyaniline, 3,4-Methylenedioxyphenol, 2-Methyl-5-Hydroxyethylaminophenol, Methylimidazoliumpropyl p-Phenylenediamine, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, p-Phenylenediamine, Phenyl-Methyl-Pyrazolone, N-Phenyl-p-Phenylenediamine, Picramic Acid, Pyrocatechol, Pyrogallol, Resorcinol, Sodium Picramate, Tetraaminopyrimidine, Tetrahydro-6-Nitroquinoxaline, Tetrahydropyranyl, Resorcinol, Toluene-2,5-Diamine, Toluene-2,6-Diamine, Toluene-3,4-Diamine, 2,5,6-Triamino-4-Pyrimidinol, 1,2,4-Trihydroxybenzene. Oxidative dyes can be in the form of salts.

All these components are well known to the expert in the field and belong to his/her general knowledge. The above-mentioned components are commercially available or can be prepared by known methods described in the literature.

The chemical names are also well understood by the expert, although the above-mentioned components can also be known by other common, commercial or IUPAC names.

The total amount of the combination of the primary colourants and couplers in the dye according to the invention is conventionally determined by the expert in the art. For example, said amount preferably varies from about 0.001 to 20 wt. %, more preferably from about 0.01 to 6.0 wt. %.

When the hair dye is mixed with the activator, which in most cases is acidic (pH of from about 2 to 6.5), the pH of the ready-to-use dyes of the invention assumes a value determined by the amount of alkali in the dye and by the amount of acid in the oxidant as well as by the mixing ratio. Depending on the composition, the ready-to-use dyes of the invention can be slightly acidic, neutral or alkaline and have a pH of from about 3 to 11, preferably from 6.5 to 11.

The meaning of the term "activator" is clear to the expert in the field; it refers, for example, to hydrogen peroxide, carbamide peroxide, perborates and persulfates or peracids, preferably hydrogen peroxide. The amount can vary between 0.1 and 50%.

Examples of direct colourants, as defined according to the INCI nomenclature, comprise:
Acid green 25, Acid blue 74, Acid blue 3, Acid blue 9, Acid red 18, Acid red 184, Acid red 195, Acid red 27, Acid red 33, Acid red 35, Acid red 51, Acid red 73, Acid red 87, Acid red 92, Acid red 95, Acid violet 43, Acid violet 9, Acid yellow 23, Acid yellow 3, Acid yellow 36, Acid yellow 73, Acid orange 6, Acid orange 7, Acid green 1, Acid green 50, Acid Blue 1, Acid Blue 62, Acid Brown 13, Acid Orange 3, Acid Orange 24, Acid Red 14, Acid Red 35, Acid Red 52, Acid Yellow 1, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 3, Basic Blue 7, Basic Blue 9, Basic Blue 26, Basic Blue 47, Basic Blue 75, Basic Blue 99, Basic Brown 4, Basic Brown 16, Basic Brown 17, Basic Green 1, Basic Green 4, Basic Orange 1, Basic Orange 2, Basic Orange 31, Basic Red 1, Basic Red 1:1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11:1, Basic Violet 14, Basic Violet 16, Basic Yellow 28, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Brown 1, Disperse Orange 3, Disperse Red 11, Disperse Red 15, Disperse Red 17, Disperse Violet 1, Disperse Violet 4, Disperse Violet 15, HC Blue No 2, HC Blue No 5, HC Blue No 6, HC Blue No 9, HC Blue No 10, HC Blue No 11, HC Blue No 12, HC Blue No 13, HC, HC Blue No 15, HC Blue No 18, HC Brown No 1, HC Brown No 2, HC Green No 1, HC Orange No 1, HC Orange No 2, HC Orange No 3, HC Orange No 5, HC Orange No 6, HC Red No 1, HC Red No 3, HC Red No 7, HC Red No 8, HC Red No 9, HC Red No 10, HC Red No 11, HC Red No 13, HC Red No 14, HC Red No 15, HC Red No 17, HC Red No 18, HC Violet No 1, HC Violet No 2, HC Yellow No 2, HC Yellow No 4, HC Yellow No 5, HC Yellow No 6, HC Yellow No 7, HC Yellow No 8, HC Yellow No 9, HC Yellow No 10, HC Yellow No 11, HC Yellow No 12, HC Yellow No 13, HC Yellow No 14, HC Yellow No 15, HC Yellow No 16, HC Yellow No 17, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl-Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl-Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline, Tetrahydropyranyl Resorcinol.

Furthermore, the colourants described in WO 2014202152 can also be used.

The total amount of the combination of the primary colourants and couplers in the dye according to the invention is conventionally determined by the expert in the field. For example, the total amount of direct colourant in the dye according to the invention varies preferably from about 0.001 to 20 wt. %, more preferably from about 0.002 to 10 wt. % and even more preferably from about 0.01 to 6.0 wt. %.

Examples of direct natural colourants comprise those based on lawsone, juglone, alizarin, purpurin, carminic acid, kermesic acid, purpurogallin, protocatecaldehyde, indigo, isatin, curcumin, spinulosin and apigeninidin. Extracts or decoctions containing these natural colourants can also be used, in particular henna-based packs or extracts.

The composition can also comprise other components known in the sector, for example ingredients for improving the intensity and life of the colour, such as a compound formed by the esterification of the phosphoric acid with isooctanol and ethoxylated tridecylic alcohol, defined in the INCI nomenclature as Potassium Ethylhexyl/Isotrideceth-8 Phosphate. The amount of the ingredient is determined by the expert based on his/her experience, for example, the above-mentioned Potassium Ethylhexyl/Isotrideceth-8 Phosphate is present in an amount of from 0.1 to 20 wt. %, preferably from 0.2 to 10 wt. %.

The composition can also comprise a pH corrector chosen, for example, from ammonia, monoethanolamine (MEA), 1-amino-2-propanol, 2-amino-2-methyl-propanol (AMP), 2-amino-2-methyl-1,3-propanediol, 2-amino-2-ethyl-1,3-propanediol, tris(hydroxymethyl)-aminomethane (tromethamine, Tris), sodium hydroxide, potassium hydroxide, urea, allantoin, arginine, tripotassium phosphate, sodium saccharin, triethanolamine (TEA), lactic acid, citric acid, phosphoric acid or combinations thereof.

In this case, too, the total amount of the corrector is conventionally determined by the expert in the art; for example, the amount of pH corrector can vary from 0.1 to 20 wt. %, preferably from 0.2 to 10 wt. %.

Alkanolamine can be present in the form of a free base or a salt.

In accordance with the invention, pigments can also be used, for example iron oxides, titanium oxides, zinc oxides, chromium oxides, ultramarine, manganese violet, or ferric ferrocyanide. Other particular pigments that can be used are those marketed under the name WATERSPERSE® (S.A COLOR); UNIPURE® (SENSIENT); CELLINI® (BASF); DISTINCTIVE® (RE SOURCE OF NATURE); COLORONA® (MERCK); WD (DAITO KASEI).

These pigments can be included in the composition in absolutely conventional amounts, for example from 0.01 to 10 wt. % of the total weight of the composition, preferably from 3 to 8%.

The hair dyes of the invention can also contain one or more natural or synthetic additives, commonly used in solutions, creams, emulsions, gels, aerosols, foams, powders and granulates, for example solvents, such as: water, low molecular weight aliphatic mono or polyalcohols, their esters and ethers, for example alkanols, in particular having from 1 to 4 carbon atoms, such as ethanol, n-propanol, isopropanol, butanol, isobutanol; bivalent or trivalent alcohols, in particular having from 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerol, diethylene glycol, dipropylene glycol, polyalkylene glycols, such as triethylene glycol, polyethylene glycol, tripropylene glycol and polypropylene glycol; low molecular weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having between 3 and 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropyl ether; esters such as ethyl formate, methyl formate, methyl acetate, ethyl acetate, propyl acetate, butyl acetate, phenyl acetate, ethylene glycol monoethyl ether acetate or acetic acid hydroxy ethyl ester; amides such as N-methyl-pyrrolidone; such as pure urea, tetramethyl urea and thiodiglycol; furthermore, humectants or emulsifiers chosen from anionics, cationics, non-ionogenics, amphoterics or zwitterionics, surfactant substances, such as fatty alcohol sulfates, alkyl sulfonates, alkylbenzene sulfonates, salts of alkyltrimethylammonium, alkyl betaine, α-olefin sulfonates, fatty alcohol ethoxylates, nonylphenol ethoxylates, fatty acid alkanolamines, ethoxylated esters of fatty acids, polyglycol ether sulfates of fatty acids, alkyl polyglycosides; thickeners, such as higher fatty alcohols, amide, cellulose derivatives, petroleum jelly, paraffin oil, fatty acids and other fatty components in emulsified form, polymeric water-soluble thickeners, for example natural gums, guar gum, xanthan gum, carob flour, pectin, dextran, agar-agar, amylose, amylopectin, dextrin, clays or synthetic hydrocolloids, such as polyvinyl alcohol; conditioning agents, such as lanolin derivatives, cholesterol, pantothenic acid, water-soluble cationic polymers, protein derivatives, provitamins, vitamins, plant extracts, sugar and betaine; auxiliary agents, such as electrolytes, antioxidants, sequestrants, film-forming agents and preservatives such as beeswax.

In this case, it can be particularly advantageous to add to the dyes surfactants or non-ionic and/or anionic emulsifiers, such as fatty alcohol sulfates, in particular lauryl sulfate, sodium cocoyl sulfate, fatty alcohol ethoxylate sulfates, in particular sodium lauryl ether sulfates having between 2 and 4 molecular units of ethylene oxide, fatty acid ethoxylate esters, nonylphenol ethoxylates, fatty alcohol ethoxylates, alkylbenzene sulfonates or fatty acid alkanolamides, amounting in total to preferably from about 0.1 to 30 wt. %, more preferably from 0.2 to 15 wt. %.

Examples of useful cationic surfactants are composed of quaternary ammonium, ammonium halides such as alkyl trimethyl ammonium chlorides, dialkyl dimethyl ammonium chlorides and trialkyl methyl ammonium chlorides. Specific examples are cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other useful cationic surfactants are quaternised protein hydrolysates.

As well as non-ionic organic thickeners with wax-like properties and non-ionic surfactants, the dye can comprise the customary cosmetic cationic resins. Particularly preferred are Polyquaternium-6 (poly(dimethyl-diallyl ammonium chloride)), Polyquaternium-7 (diethyl diallyl ammonium chloride/acrylamide copolymer), Polyquaternium-10 (cationic cellulose), Polyquaternium-11 (diethyl sulfate of N,N-dimethylaminoethyl methacrylic acid/PVP copolymer), Polyquaternium-22, Polyquaternium-35 and Polyquaternium-37 (trimethylaminoethyl methacrylate chloride polymer), alone or mixtures thereof. The total amount of cationic resins in the dye can be from about 0.1 to 6 wt. %.

A method for dyeing hair comprising the direct application on the hair of the composition of the invention is also within the scope of the present invention. The combination can be used directly on the hair in the form of any cosmetic formulation which may have different pH values (from 0.5 to 14). The correct amount of product is applied to the hair and left on typically for between a few seconds and 60 minutes. The application time is easily determined by the expert on the basis of his/her knowledge and experience.

A further exemplary method for dyeing hair according to the invention comprises the following steps:
a) mixing of the composition of the invention with a cosmetic hair product;
b) subsequent application to the hair;
c) subsequent rinse;
d) optional washing with shampoo; and, if desired,
e) drying.

The combination can be mixed at the moment of use with a wide range of hair cosmetic products such as a mask, typically having a pH of 3-5; a shampoo, typically having a pH of 6-7; an activator or a neutraliser with hydrogen peroxide typically having a pH of 2-6.5; an oxidative hair dye, typically having a pH of 9-11; a semi-permanent straightener preferably based on alpha-keto acids or alpha-hydroxy acids, typically having a pH of 0.5-2; a composition for hair styling typically having a pH of 7; a highly alkaline (typically having a pH of 11-12) or thioglycolate-based (typically having a pH of 9.5) permanent straightener.

The composition according to the present invention is prepared in a conventional manner, according to general knowledge in the field. By way of example, reference can be made to the *Manuale delle preparazioni cosmetiche e dermatologiche* [*Manual of cosmetic and dermatological preparations*], Tecniche Nuove [New Technologies], 2013 (ISBN 8848127010, 9788848127011), *Introduction to Cosmetic Formulation and Technology*, Wiley, 2015.

As mentioned, and this represents one of the advantages of the present invention, the composition described here is highly versatile and can be used alone, or can be added to any other cosmetic, in particular a cosmetic for hair, for example shampoo, lotion, conditioner, other dye, hair care and maintenance compositions, hairstyling compositions, without the various pH values of the cosmetic influencing the features of the colourant composition of the present invention. In particular, the compositions of the present invention are stable at the various pH values, maintain their characteristic shade and brilliance, and withstand washing.

In a preferred embodiment, the composition of the present invention is suitable for use in what are known as ready-to-use formulations. Such a formulation essentially comprises three components: a) the colourant composition of the present invention, b) an oxidative dye, c) an oxidant for the colourant b). The components can be supplied separately, where a technician in the field will prepare the dye at the time, or can be included in a single kit, optionally with the appropriate use instructions for mixing and applying them.

For using semi-permanent straighteners, reference is made to compounds of the general formula:

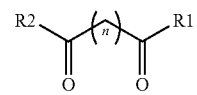

wherein $R_1$ and $R_2$ can be hydrogen, hydroxyl, amine or a $C_1$-$C_{10}$ alkyl group. The number of carbon atoms n can be from 0 to 10 with possible unsaturations or amine groups, which are optionally substituted by an alkyl having from 1 to 4 carbon atoms, ketones or hydroxyls therewithin. Preferably, this refers to glyoxylic acid, pyruvic acid, maleic acid, and amides or esters of glyoxylic acid, pyruvic acid and maleic acid. The composition of the present invention can be included directly in the straightening product or mixed at the time of use.

The invention can be mixed with an ammonium thioglycolate-based formulation just before application to the hair, or added directly to the formulation for straightening or curling the hair and at the same time colouring it in a single application.

The hair dye of the invention provides an intensive, protective and gentle colouring. On account of the improved colour balance, hair dyeing can be carried out from the undamaged hairline up to severely damaged tips.

The invention is further illustrated by the following examples, where the various qualitative/quantitative evaluations have been produced either by using equipment, or by experts in the field (colour technicians).

The results of the shade expressed in L*a*b* values obtained by the following examples were measured using a Minolta Chroma Meter CR-200 colorimeter.

In the L*a*b* colour space, L* indicates brightness while a* and b* are the chromaticity coordinates. a* and b* indicate colour directions: +a* is the red direction, −a* is the green direction, +b* is the yellow direction and −b* is the blue direction.

Colour differences can be expressed by ΔE values, which are defined by the following equation:

$$\Delta E=[(\Delta L^-)^2+(\Delta a^-)^2+(\Delta b^-)^2]^{1/2}$$

EXAMPLES

The components shown in the examples are named according to the INCI nomenclature.

The compositions used for the examples shown are described in Table 2.

TABLE 2

Composition A (combination of BB124 with HC BLUE 16) is the one according to the invention. Compositions B, C, D and E comprise only one blue colourant. Composition F (combination of BB124 with HC BLUE 2) is not within the scope of the present invention and it is used for a comparison with the state of the art.

| INGREDIENTS (INCI) | A w/wt. % | B w/wt. % | C w/wt. % | D w/wt. % | E w/wt. % | F w/wt. % |
|---|---|---|---|---|---|---|
| WATER | Qs 100 | Qs 100 | Qs 100 | Qs 100 | Qs 100 | Qs 100 |
| CETEARYL ALCOHOL | 10 | 10 | 10 | 10 | 10 | 10 |
| SODIUM LAURETH SULFATE | 1.5 | 1.5 | 1.5 | 1.5 | 1.5 | 1.5 |
| LAURETH-3 | 2 | 2 | 2 | 2 | 2 | 2 |
| GLYCERYL STEARATE SE | 0.5 | 0.5 | 0.5 | 0.5 | 0.5 | 0.5 |
| PARFUM | 0.5 | 0.5 | 0.5 | 0.5 | 0.5 | 0.5 |
| CERA ALBA | 0.5 | 0.5 | 0.5 | 0.5 | 0.5 | 0.5 |
| BASIC BLUE 124 | 0.1 | — | 0.4 | 0.1 | — | 0.1 |
| HC BLUE 16 | 0.3 | 0.4 | — | — | 0.3 | — |
| HC BLUE 2 | — | — | — | — | — | 0.3 |
| HYDROXYETHYLCELLULOSE | 0.4 | 0.4 | 0.4 | 0.4 | 0.4 | 0.4 |
| EDTA | 0.3 | 0.3 | 0.3 | 0.3 | 0.3 | 0.3 |
| *LIMNANTHES ALBA* SEED OIL | 0.2 | 0.2 | 0.2 | 0.2 | 0.2 | 0.2 |

Example 1

Table 3 shows the values of % colour loss after 6 washes on bleached hair. Compositions A, B, and C were applied to the hair and left on for 30 minutes at a temperature of 30° C. The hair was then rinsed and dried.

TABLE 3

Comparison of compositions applied on bleached hair after 6 washes.

|  | % loss of Eab |
|---|---|
| Composition A | 18% |
| Composition B | 26% |
| Composition C | 22% |

Example 2

Table 4 shows the difference in colour achieved at various pH values for compositions A, D, E and F using methods 1, 2 and 3, described below.

TABLE 4

Comparison of compositions A, D, E and F at various pH values

| Composition | Colour at pH 0.8 (glyoxylic acid) with method 1 | Colour at pH 6 with method 2 | Colour at pH 11 with method 3 |
|---|---|---|---|
| A | Brilliant blue | Brilliant blue | Brilliant blue |
| D | Blue-green | Dark blue | Pale violet |
| E | Pale blue | Blue-Lavender | Blue-Lavender |
| F | Intense Blue | Intense Blue | Violet-brown |

As evident from the above Table 4, composition A according to the invention is the only one which is able to maintain a brilliant blue colouring at all the tested pH values. Differently, compositions D, E and F provide a colouring which changes at different pH values. In particular, it is noteworthy that composition F, which comprises two blue dyes but not according to the present invention, provides a blue colouring which shades to violet-brown at basic pH.

Method 1: Each composition mentioned above, A, D, E and F was mixed in a 1:1 ratio with a solution at a pH of 0.8 of glyoxylic acid. The ready-to-use mixture was applied to locks of blond hair and left on for 30 minutes, then rinsed and straightened at 230° C. using a hair straightener. The locks were rinsed and dried.

Method 2: Each composition mentioned above A, D, E and F at a pH of 6, was applied to the hair for 30 minutes and then rinsed and dried.

Method 3: Each composition mentioned above A, D, E and F, was mixed in a 1:1 ratio with an oxidative hair dye and a 40 volume activator (for example 5 g composition A, 5 g ALFAPARF EVOLUTION CUBE 0Sp dye and 15 g ALFAPARF OXID'O ACTIVATOR 40V).

Tables 5 and 6 show further examples of compositions according to the invention. These combinations can be used alone, directly on the hair, or mixed with other products in a ready-to-use mixture for application to the hair.

TABLE 5

| | Composition: | | | | | | | | |
|---|---|---|---|---|---|---|---|---|---|
| INGREDIENTS (INCI) | D w/w % | E w/w % | F w/w % | G w/w % | H w/w % | I w/w % | L w/w % | M w/w % | N w/w % |
| WATER | Qs 100 | Qs 100 | Qs 100 | Qs 100 | Qs 100 | Qs 100 | Qs 100 | Qs 100 | Qs 100 |
| CETEARYL ALCOHOL | 10 | 10 | 10 | 10 | 10 | — | — | — | — |
| LAUROYL/MYRISTOYL METHYL GLUCAMIDE | 1.5 | 1.5 | 1.5 | 1.5 | 1.5 | 5 | 5 | 5 | 5 |

TABLE 5-continued

| | Composition: | | | | | | | | |
|---|---|---|---|---|---|---|---|---|---|
| INGREDIENTS (INCI) | D w/w % | E w/w % | F w/w % | G w/w % | H w/w % | I w/w % | L w/w % | M w/w % | N w/w % |
| ETHANOLAMINE | 0.1 | 0.1 | 0.1 | 0.1 | 0.1 | 0.1 | 0.1 | 0.1 | 0.1 |
| COCAMIDOPROPYL BETAINE | 0.2 | — | — | — | — | 5 | 5 | 5 | 5 |
| HYDROXYETHYLCELLULOSE | — | — | — | — | — | 1 | 1 | 1 | 1 |
| SODIUM LAURYL SULFATE | — | — | — | — | 0.5 | — | — | — | — |
| LAURETH-3 | 2 | 2 | 2 | 2 | 2 | 2 | 2 | 2 | 2 |
| Potassium Ethylhexyl/Isotrideceth-8 Phosphate | 1.5 | 2 | 0.5 | 2.5 | 10 | 10 | 10 | 10 | 10 |
| GLYCERYL STEARATE SE | 0.5 | 0.5 | 0.5 | 0.5 | 0.5 | 0.5 | 0.5 | 0.5 | 0.5 |
| PARFUM | 0.6 | 0.6 | 0.6 | 0.6 | 0.6 | 0.6 | 0.6 | 0.6 | 0.6 |
| CERA ALBA | 0.5 | 0.5 | 0.5 | 0.5 | 0.5 | 0.5 | 0.5 | 0.5 | 0.5 |
| PENTASODIUM PENTETATE | — | 0.3 | 0.3 | — | — | 0.3 | 0.3 | 0.3 | 0.3 |
| ERYTHORBIC ACID | 0.4 | 0.4 | 0.4 | 0.4 | 0.4 | 0.4 | 0.4 | 0.4 | 0.4 |
| EDTA | 0.1 | — | — | — | — | — | — | — | — |
| *LIMNANTHES ALBA* SEED OIL | 0.2 | 0.2 | 0.2 | 0.2 | 0.2 | 0.2 | 0.2 | 0.2 | 0.2 |
| BASIC RED 51 | — | 1 | 0.2 | — | — | 0.1 | 0.1 | 0.1 | 0.1 |
| BASIC YELLOW 87 | — | 0.5 | 0.4 | — | — | 0.6 | 0.6 | 0.6 | 0.6 |
| BASIC YELLOW 57 | — | — | — | 1 | — | — | — | — | — |
| BASIC ORANGE 31 | — | 0.3 | — | — | — | — | — | — | — |
| BASIC BLUE 124 | 0.1 | 0.5 | 0.05 | 0.1 | 0.1 | 0.5 | 0.05 | 0.1 | — |
| HC BLUE 16 | 0.5 | 3 | — | 0.5 | 0.5 | 0.5 | — | 0.05 | — |
| HC BLUE 17 | 0.2 | — | 0.5 | — | — | — | — | — | — |
| HC BLUE 4 | — | — | — | — | — | — | 0.5 | 0.6 | — |
| DISPERSE BLUE 359 | — | — | — | — | — | — | — | 0.4 | — |
| HC BLUE 8 | — | — | — | — | — | — | — | 0.1 | 0.5 |
| BASIC BLUE 75 | — | — | — | — | — | — | 0.1 | — | 0.3 |
| ACID RED 92 | 0.05 | — | — | — | — | — | — | — | — |
| ACID RED 52 | 0.05 | — | — | — | — | — | — | — | — |
| HC BLUE 2 | 0.1 | — | — | — | 1 | 1 | 1 | 1 | 1 |
| HC BLUE 18 | 0.1 | — | — | 0.2 | — | — | — | — | — |
| HC RED 18 | 0.1 | — | — | 0.3 | — | — | — | — | — |
| 3-NITRO-p-HYDROXY-ETHYLAMINOPHENOL | — | — | — | — | 1 | 1 | 1 | 1 | 1 |
| GLYOXYLIC ACID | 15 | — | — | — | 15 | — | — | — | — |
| MALEIC ACID | — | 20 | — | — | — | — | — | — | — |
| PYRUVIC ACID | — | — | 23 | — | — | — | — | — | — |
| GLYOXYLOYL CYSTEINE | 1 | — | — | 10 | — | 15 | 15 | 15 | 15 |
| GLYOXYLOYL CARBOCYSTEINE | 5 | — | — | — | — | — | — | — | — |
| GLYOXYLOYL HYDROLYZED WHEAT PROTEIN/SERICIN | 5 | — | — | — | — | — | — | — | — |
| GLYOXYLOYL KERATIN AMINO ACIDS | 4 | — | — | — | — | — | — | — | — |
| SODIUM GLYOXYLATE | 5 | — | — | — | 2 | 2 | 2 | 2 | 2 |
| DIMETHYL ISORBIDE | 5 | 1 | 2 | 3 | 2 | 1 | 1 | 1 | 1 |

TABLE 6

| INGREDIENTS (INCI) | O w/wt % | P w/wt % | Q w/wt % | R w/wt % | S w/wt % | T w/wt % | U w/wt % | V w/wt % | Z w/wt % | AA w/wt % | AB w/wt % | AC w/wt % | AD w/wt % |
|---|---|---|---|---|---|---|---|---|---|---|---|---|---|
| WATER | Qs 100 | Qs 100 | Qs 100 | Qs 100 | Qs 100 | Qs 100 | Qs 100 | — | — | — | Qs 100 | Qs 100 | Qs 100 |
| CETEARYL ALCOHOL | 10 | 10 | — | — | — | — | — | — | — | — | 10 | 10 | 10 |
| CETEARETH-20 | 4 | 3 | — | — | — | — | — | — | — | — | 4 | 4 | 4 |
| SODIUM LAURETH SULFATE | — | — | 10 | 1 | — | — | — | — | — | — | — | — | — |
| LAUROYL/MYRISTOYL METHYL GLUCAMIDE | — | — | 10 | 10 | — | — | — | — | — | — | — | — | — |
| ETHANOLAMINE | 0.5 | — | — | — | — | 0.5 | — | — | — | — | 0.5 | 0.5 | 0.5 |
| CETRIMONIUM CHLORIDE | 2 | 2 | — | — | 1 | 1 | — | — | — | — | 2 | 2 | 2 |
| COCAMIDOPROPYL BETAINE | — | — | — | 5 | 1 | 1 | 2 | — | — | — | — | — | — |
| SODIUM LAURYL SULFATE | — | 0.5 | 0.5 | 0.5 | — | — | — | — | — | — | — | — | — |
| LAURETH-3 | — | 2 | — | — | — | — | — | — | — | — | — | — | — |
| HYDROXYETHYLCELLULOSE | 0.2 | 0.2 | 0.2 | 0.5 | 1.5 | 1.5 | 0.2 | 0.5 | 0.5 | 0.5 | 0.2 | 0.2 | 0.2 |
| GELLAN GUM | — | — | 0.05 | 0.1 | — | — | — | 4 | 4 | 4 | — | — | — |
| POTASSIUM ETHYLHEXYL/ISOTRIDECETH-8 PHOSPHATE | 1 | 1.5 | 1 | 0.5 | — | — | 2 | — | — | — | 1 | 1 | 1 |
| GLYCERYL STEARATE SE | — | 0.5 | 0.5 | 0.5 | — | — | — | — | — | — | — | — | — |
| PARFUM | 0.5 | 0.5 | 0.5 | 0.5 | 0.5 | 0.5 | 0.5 | 0.2 | 0.2 | 0.2 | 0.5 | 0.5 | 0.5 |
| CERA ALBA | 0.5 | 0.5 | 0.5 | 0.5 | — | — | — | — | — | — | 0.5 | 0.5 | 0.5 |
| ERYTHORBIC ACID | 0.4 | 0.4 | 0.4 | 0.4 | — | — | — | — | — | — | 0.4 | 0.4 | 0.4 |
| EDTA | 0.3 | 0.3 | 0.3 | 0.3 | — | — | 0.3 | — | — | — | 0.3 | 0.3 | 0.3 |

TABLE 6-continued

| INGREDIENTS (INCI) | O w/wt % | P w/wt % | Q w/wt % | R w/wt % | S w/wt % | T w/wt % | U w/wt % | V w/wt % | Z w/wt % | AA w/wt % | AB w/wt % | AC w/wt % | AD w/wt % |
|---|---|---|---|---|---|---|---|---|---|---|---|---|---|
| SODIUM SULFATE | — | — | — | — | — | — | 0.1 | — | — | — | — | — | — |
| *LIMNANTHES ALBA* SEED OIL | 0.2 | 0.2 | 0.2 | 0.2 | 0.2 | 0.2 | — | — | — | — | 0.2 | 0.2 | 0.2 |
| SODIUM POLYACRYLATE | — | — | — | — | — | — | 0.5 | — | — | — | — | — | — |
| CARBOMER | — | — | — | — | — | — | 0.5 | — | — | — | — | — | — |
| ACRYLATES/METHACRYLAMIDE COPOLYMER | — | — | — | — | — | — | 0.2 | — | — | — | — | — | — |
| BASIC RED 51 | — | 0.5 | — | 0.03 | — | 0.2 | — | 0.2 | — | — | — | — | — |
| BASIC YELLOW 87 | — | 1 | — | 0.01 | — | 0.7 | — | 0.3 | — | — | — | — | — |
| BASIC YELLOW 57 | — | — | — | — | — | 0.1 | — | — | — | — | — | — | — |
| BASIC ORANGE 31 | — | 0.2 | — | — | — | — | — | — | — | — | — | — | — |
| BASIC BLUE 124 | 0.1 | 0.1 | 0.05 | 0.1 | 0.1 | 0.1 | 0.1 | 0.1 | 0.1 | 0.1 | 0.05 | 0.01 | 0.005 |
| HC BLUE 16 | 0.3 | — | 0.02 | 0.3 | 0.3 | 0.3 | 0.3 | 0.3 | 0.3 | 0.3 | 0.1 | — | 0.03 |
| HC BLUE 17 | — | 0.8 | — | — | — | — | — | — | — | — | — | — | — |
| ACID RED 92 | — | — | 0.1 | — | — | — | — | — | — | — | — | — | — |
| ACID RED 52 | — | — | — | 0.1 | — | — | — | — | — | — | — | — | — |
| HC BLUE 2 | — | — | — | — | 0.5 | — | — | — | — | — | — | — | — |
| HC BLUE 18 | — | — | — | — | — | 0.3 | — | — | — | — | — | — | — |
| HC BLUE 4 | — | — | — | — | — | — | — | — | — | — | 0.5 | — | — |
| DISPERSE BLUE 359 | — | — | — | — | — | — | — | — | — | — | — | — | 0.3 |
| HC BLUE 8 | — | — | — | — | — | — | — | — | — | — | — | 0.6 | 0.1 |
| BASIC BLUE 75 | — | — | — | — | — | — | — | — | — | — | 0.5 | 0.3 | 0.4 |
| HC RED 18 | — | — | — | — | — | 0.2 | — | — | — | — | — | — | — |
| 3-NITRO-p-HYDROXY-ETHYLAMINOPHENOL | — | — | — | — | 0.2 | — | — | — | — | — | — | — | — |
| TIN OXIDE | — | — | 1 | 1 | — | — | — | — | — | — | — | — | — |
| IRON OXIDE | — | 2 | 2 | 2 | — | — | — | — | — | — | — | — | — |
| MICA | — | — | 2 | 2 | 2 | — | — | — | — | — | — | — | — |
| TITANIUM DIOXIDE | — | — | 2 | 2 | 2 | — | — | — | — | — | — | — | — |
| CYSTEINE | — | — | 0.5 | 0.5 | 0.5 | — | — | — | — | — | — | — | — |
| ALLANTOIN | — | — | 0.5 | 0.5 | 0.5 | — | — | — | — | — | — | — | — |
| KAOLIN | — | — | — | — | — | — | — | Qs 100 | Qs 100 | Qs 100 | — | — | — |
| SILICATE or METASILICATE | — | — | — | — | — | — | — | 1 | 1 | 10 | — | — | — |

The invention claimed is:

1. A hair coloring composition comprising a mixture of blue dyes,
wherein the mixture of blue dyes provides a blue hair coloring which is stable at any pH value, and the mixture of blue dyes consists of:
a dye having the following formula (I) and a dye having the following formula (II):

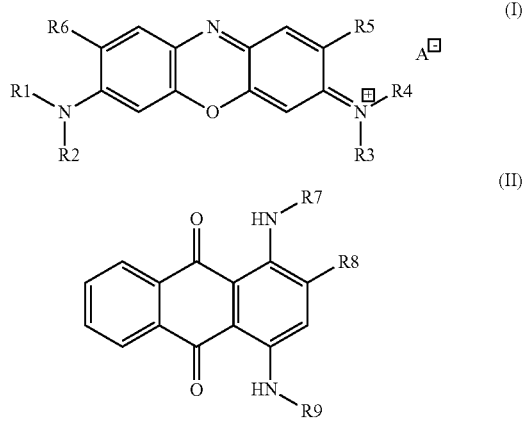

wherein,
in formula (I):
$R_1$, $R_2$, $R_3$ and $R_4$ can be a hydrogen, an alkyl group from $C_1$ to $C_{10}$, linear, branched, saturated or unsaturated or an aryl group; when each of the $R_1$-$R_4$ groups is a $C_1$-$C_{10}$ alkyl chain, this can be substituted by one or more amino, imino, hydroxyl and aldehyde groups, and/or this chain can contain one or more nitrogen groups, optionally substituted by a $C_1$-$C_6$ alkyl group, linear or branched, saturated or unsaturated; oxygen, keto; $R_5$ is hydrogen or a $C_1$-$C_6$ alkoxy group, linear or branched, saturated or unsaturated, $R_6$ is hydrogen or a linear or branched alkyl group in which hydroxyl groups or amino groups can be present, said amino groups optionally substituted with an alkyl from 1 to 4 atoms of carbon,
A is a cosmetically acceptable anion;
in formula (II):
$R_7$, $R_8$ and $R_9$ are independently hydrogen, an alkyl group from $C_1$ to $C_{10}$, linear or branched, saturated or unsaturated, an aryl group, a cyano group; when each of the $R_7$-$R_9$ groups is a $C_1$-$C_{10}$ alkyl chain, this can be optionally substituted by one or more amino, imino, hydroxyl and aldehyde groups, and/or said chain can optionally contain one or more nitrogen groups, optionally substituted by a $C_1$-$C_6$ alkyl group, linear or branched, saturated or unsaturated; oxygen, keto; and their cosmetically acceptable salts,
with the proviso that when $R_8$ is H, $R_7$ and $R_9$ are not both selected from $CH_2CH_2OH$ and $CH_2CH_2CH_2OH$,
and the hair coloring composition further comprises:
(a) a potassium ethylhexyl/isotrideceth-8 phosphate;
(b) an oxidizing dye; or
(c) an oxidizing dye and an activator for the oxidizing dye.

2. The hair coloring composition of claim 1, wherein, in the compounds of formula (I), $R_1$ and $R_2$ are independently hydrogen, methyl or phenyl, and $R_3$ and $R_4$ are independently hydrogen or saturated alkyl from $C_1$ to $C_6$.

3. The hair coloring composition of claim 1, wherein, in the compounds of formula (II) each of $R_7$, $R_8$ and $R_9$ is independently hydrogen, methyl or linear alkyl containing one or more amino groups, optionally substituted with an alkyl from 1 to 4 atoms of carbon, or one or more hydroxyl groups.

4. The hair coloring composition of claim 3, wherein $R_8$ is hydrogen or a cyano group.

5. The hair coloring composition of claim 1, wherein the dyes of formula (I) and formula (II) are independently selected from one of the following formulas:

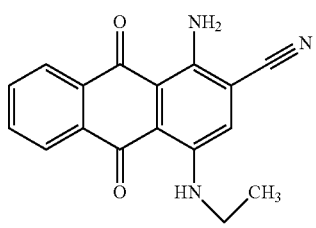

DISPERSE BLUE 359

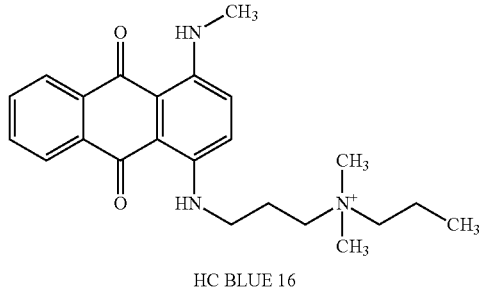

HC BLUE 16

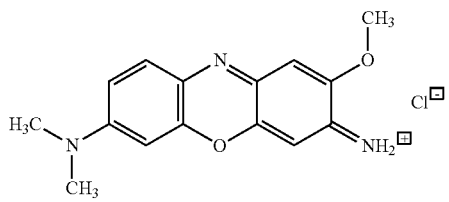

BASIC BLUE 124

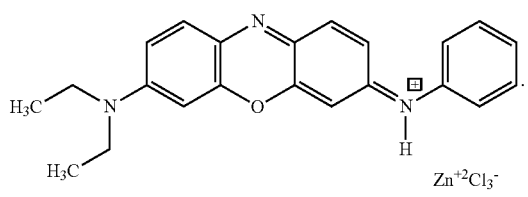

BASIC BLUE 75

6. The hair coloring composition of claim 5, wherein the dye of formula (I) is Basic Blue 124 with the formula

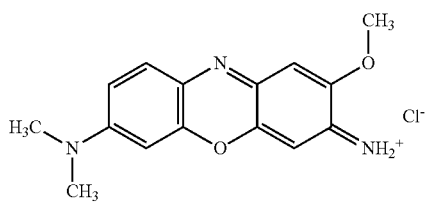

BASIC BLUE 124 and the dye of formula (II) is HC Blue 16 with the formula

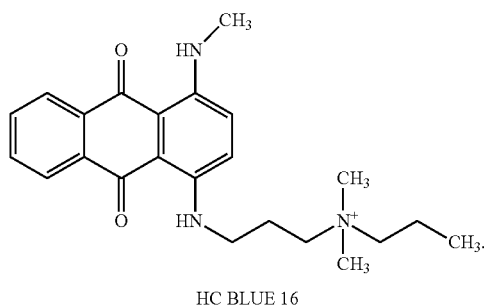 [SMILES: CCC[N+](C)(C)CCCNc1ccc(NC)c2c1C(=O)c1ccccc1C2=O]

HC BLUE 16

7. The hair coloring composition of claim 1, wherein the physiologically acceptable salt is selected from the group consisting of sulfate, hydrochloride and phosphate.

8. The hair coloring composition of claim 1, wherein the total amount of dyes of formula (I) and (II) varies from about 0.0005 to about 20% by total weight of the composition.

9. The hair coloring composition of claim 1, further comprising a non-blue hair dyes.

10. The hair coloring composition of claim 9, wherein the non-blue dye is selected from the group consisting of direct dyes, oxidative dyes, natural dyes and combinations thereof.

11. The hair coloring composition of claim 1, further comprising potassium ethylhexyl/isotrideceth-8 phosphate.

12. The hair coloring composition of claim 1, further comprising one or more of the following components: a pH corrector, pigments, natural or synthetic additives, non-ionic and/or anionic surfactants or emulsifiers, humectants, thickeners, conditioning agents, protein derivatives, provitamins, vitamins, plant extracts, sugar, betaines and auxiliary agents.

13. The hair coloring composition of claim 1, manufactured as a ready-to-use product and which further comprises:
   a. an oxidising dye; or
   b. an oxidising dye and an activator for said oxidising dye.

14. Cosmetic hair coloring product comprising the hair coloring composition of claim 1.

15. Product according to claim 14, which is in the form of or manufactured as a mask, a shampoo, an activator, a neutraliser with hydrogen peroxide, a dye, or a composition for hair styling.

16. Kit for preparing a ready-to-use composition for cosmetic hair treatment comprising the hair coloring composition of claim 1 and a cosmetic hair product.

17. The kit of claim 16 wherein said cosmetic hair product comprises a cosmetic product for dyeing hair, a hair care product, a hair styling product, an activator or a neutralizer with hydrogen peroxide,
   wherein optionally the hair care product comprises a mask or a shampoo.

18. Method for dyeing hair comprising direct application of the hair coloring composition of claim 1, wherein said method is performed at alkaline or neutral conditions.

19. Method for dyeing hair comprising the following steps:
- c. mixing the hair coloring composition of claim 1 with a cosmetic hair product;
- d. subsequent application to the hair;
- e. subsequent rinse;
- f. optional washing with shampoo; and, if desired,
- g. optional drying,
- wherein said method is performed at alkaline or neutral conditions.

20. The method of claim 18, wherein said method is performed at alkaline conditions.

21. The method of claim 19, wherein said method is performed at alkaline conditions.

22. The method of claim 18, wherein said method is performed at neutral conditions.

23. The method of claim 19, wherein said method is performed at neutral conditions.

\* \* \* \* \*